US00PP19604P2

(12) United States Plant Patent
Fankhauser

(10) Patent No.: US PP19,604 P2
(45) Date of Patent: Dec. 30, 2008

(54) APPLE TREE NAMED 'ALVINA'

(50) Latin Name: *Malus Domestica*
Varietal Denomination: Alvina

(75) Inventor: Glynn Edward Fankhauser, Drouin (AU)

(73) Assignee: Elizabeth Frankhauser, Drouin, Victoria (AU); (part interest)

( * ) Notice: Subject to any disclaimer, the term of this patent is extended or adjusted under 35 U.S.C. 154(b) by 0 days.

(21) Appl. No.: 11/879,420

(22) Filed: Jul. 16, 2007

(51) Int. Cl.
*A01H 5/00* (2006.01)

(52) U.S. Cl. ..... Plt./162
(58) Field of Classification Search ..... Plt./162
See application file for complete search history.

(56) References Cited

PUBLICATIONS

UPOV–ROM, Plant Variety Database Mar. 2006, GTI Jouve Retrieval Software, Citation for Malus 'Alvarina'one page.*

* cited by examiner

*Primary Examiner*—Annette H Para
*Assistant Examiner*—June Hwu
(74) *Attorney, Agent, or Firm*—Klarquist Sparkman, LLP

(57) ABSTRACT

A new apple variety distinguished by very high level of fruit over color, with solid flush and stripes and maturing earlier than comparator Gala selections.

3 Drawing Sheets

Latin name of the genus and species of the plant claimed: *Malus Domestica.*
Variety denomination: Alvina.

BACKGROUND OF THE INVENTION

The present invention relates to a new and distinct variety of apple tree named 'Alvina'. The new tree resulted from the discovery of a whole tree mutation in a Gala orchard in 2000. The resulting tree was selected when growing in a cultivated area in Drouin, Victoria, Australia.

BRIEF SUMMARY OF THE INVENTION

The 'Alvina' variety is distinguished from other apple varieties due to the following unique combination of characteristics: very high level of fruit over color, with solid flush and stripes and maturing earlier than comparator Gala selections.

Asexual reproduction of this new variety was performed by budding and grafting and showed that the foregoing characteristics come true to type. Asexual reproduction was performed in Drouin, Victoria, Australia.

The following detailed description concerns the original tree, 'Alvina'. The original tree and progeny have been observed growing in a cultivated area in Drouin, Victoria, Australia. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
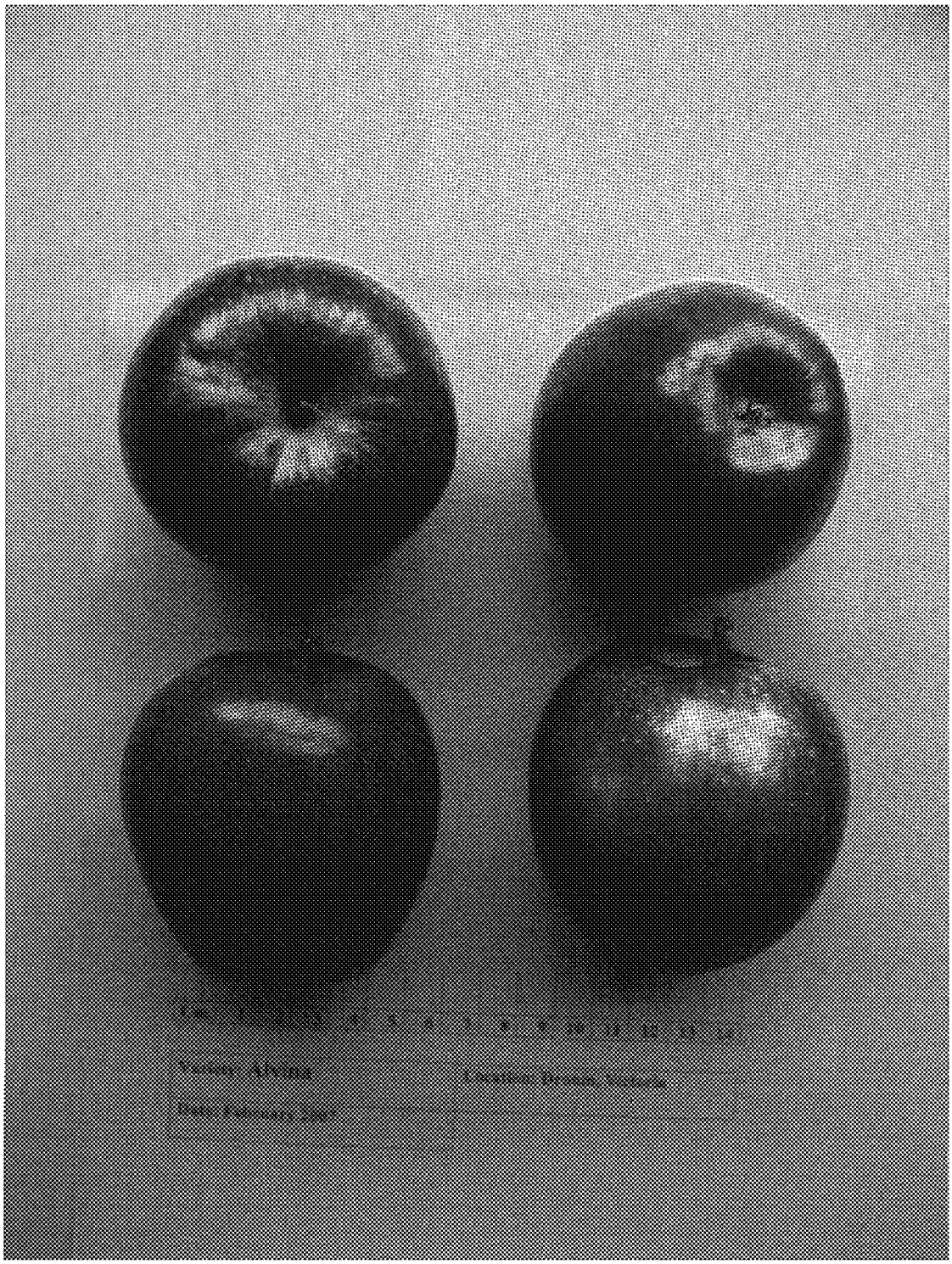
FIG. 1 is a photograph of representative apples from the 'Alvina' variety taken in February 2007 in Droulin, Victoria, Australia.
Figure 2:
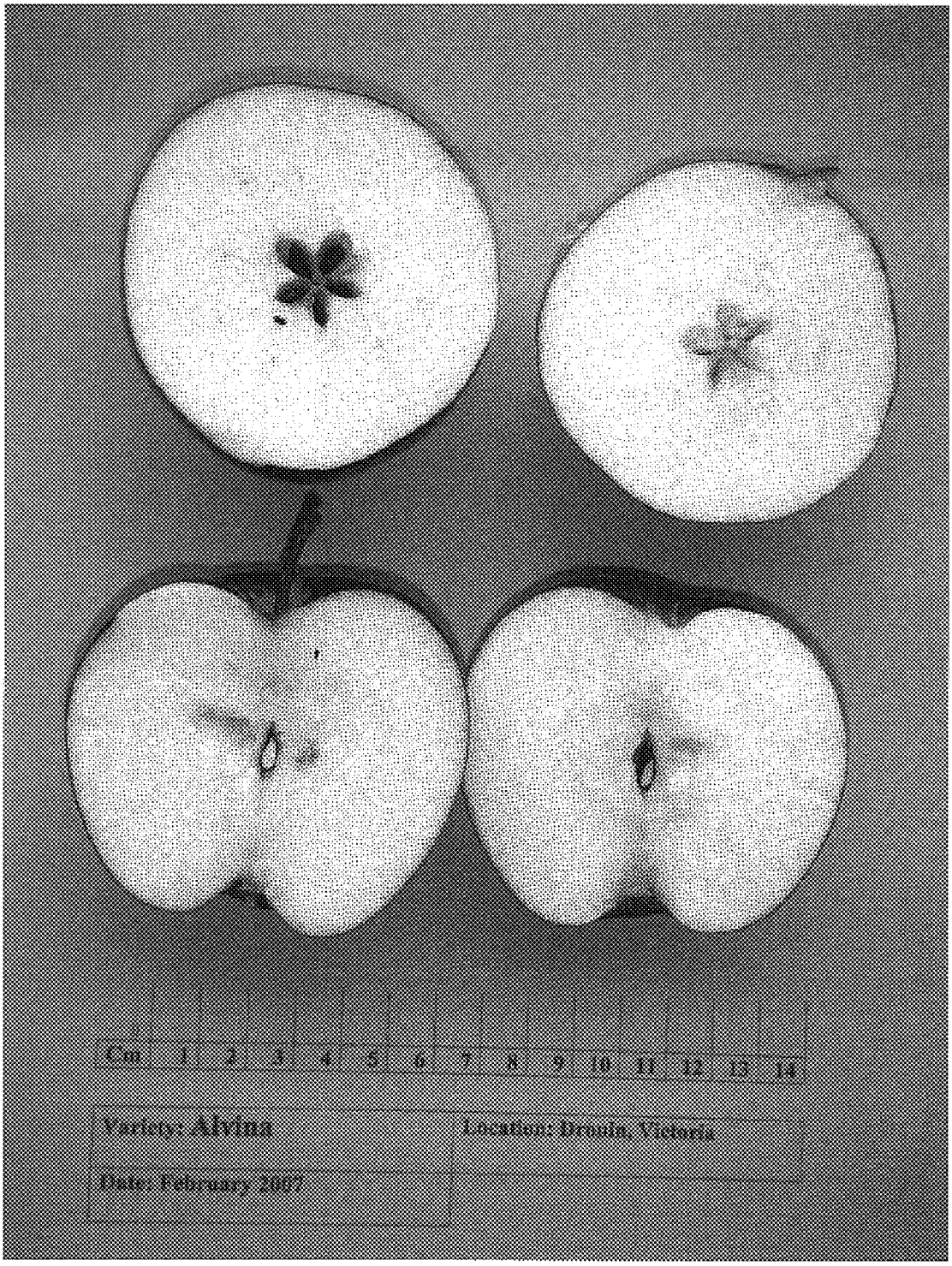
FIG. 2 is a photograph of a cross-sections of representative apples from the 'Alvina' variety taken in February 2007 in Droulin, Victoria, Australia.
Figure 3:
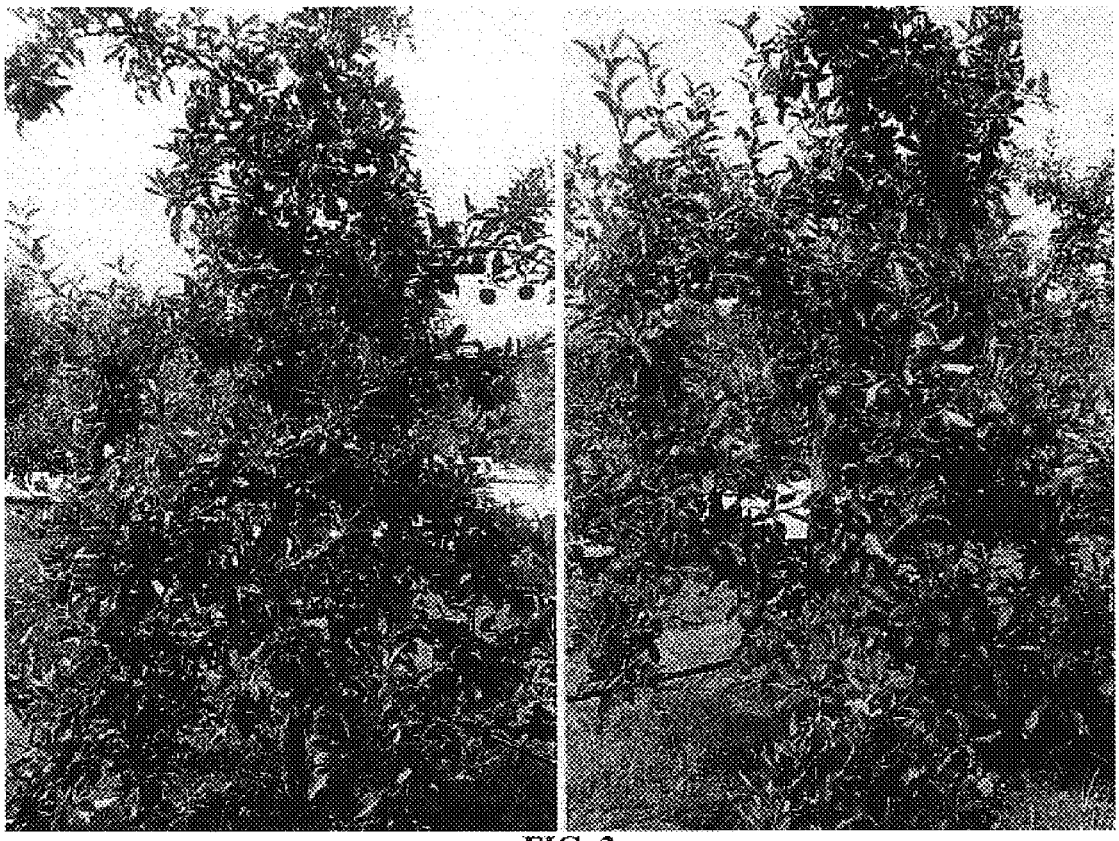
FIG. 3 is a photograph of an 'Alvina' tree bearing fruit growing in Droulin, Victoria, Australia.

The colors of an illustration of this type may vary with lighting and other conditions under which conditions and, therefore, color characteristics of this new variety should be determined with reference to the observations described herein, rather than from these illustrations alone.

DETAILED DESCRIPTION

The following detailed description of the 'Alvina' variety is based on observations of 10 trees. The observed progeny are trees which were 5 years of age and growing on M26 rootstock in the orchard in Drouin, Victoria, Australia.

Scientific name: *Malus Domestica.*
Tree:

*Vigor.*—Medium.
*Overall shape.*—Upright spreading.
*Height.*—About 8 ft.
*Width.*—Overall spread of about 4 ft.
*Caliper.*—1.4 inches.
*Trunk.*—Medium in size.
*Trunk bark texture.*—Smooth.
*New growth bark.*—Brown (RHS 200B) in color.
*Trunk bark color.*—Greyed-orange (RHS 165A).
*Patches or other markings.*—None.
*Primary branches.*—Upright and spreading.
*Branch color.*—One-year old branches and Purple (RHS N77) in color while two-year-old branches are Grey-Brown (RHS N199B) in color.
*Branch pubescence.*—Slight.
*Branch lenticels.*—Medium density, approximately 60 per square inch; on a one year old branch, typical examples of which measured about 0.04 inches in diameter; White (RHS N155A) in color.

*Internodes.*—Average internode length is about 1.0 inch on a one-year old shoot.

*Bearing.*—Annual.

*Hardiness.*—Zones, Australian and other Zones where Gala is adapted.

*Disease resistance.*—Alvina has no identified pest and disease resistances.

Leaves: (measurements were obtained from observations of ten typical leaves in autumn).

*Texture.*—Leathery.

*Sheen.*—Glossy (upper side of leaves).

*Length.*—About 4.0 inches to about 3.0 inches, averaging about 3.7 inches.

*Width.*—About 1.8 inches to about 2.3 inches, averaging about 2.1 inches.

*Thickness.*—About 0.012 inch to about 0.021 inch, averaging about 0.017 inches.

*Petiole.*—About 1.25 inches long; Greyed-Red and Yellow-Green in color (RHS 178B and RHS 148A); about 0.08 inches in diameter.

*Margin.*—Serrate.

*Tip shape.*—Acute.

*Stipules.*—2 stipules in opposite arrangement; (RHS 144A) in color; Elliptical and narrow shape; length about 0.55 inch long and about 0.1 inch wide.

*Leaf color.*—Upper leaf surface: Yellow-Green (RHS 147A). Lower leaf surface: Yellow-Green (RHS 147C). Vein: Greyed-Purple (RHS 185B).

*Pubescence.*—Light (underside of leaves).

Flowers:

*Size.*—Medium size, typical flower measuring about 1.7 inches across.

*Color.*—Unopened bud: Red-Purple (RHS 63B). Opened flower: Red-Purple (RHS 69C).

*Petals.*—5 petals per flower, oval in shape; about 0.75 (to slightly larger) inch long and 0.45 (to slightly smaller) inch wide.

*Stamen.*—Arranged in a circular row. 20 stamens, each about 0.3 inches long and White (RHS 155D) in color.

*Anthers.*—Yellow (RHS 11B) in color.

*Pistil.*—Stigma is about 0.05 inches long; 5 styles, fused at base, and Yellow-Green (RHS N144D) in color.

*Sepals.*—About 0.35 inches long and about 0.15 inches wide; narrow acute in shape, Green (RHS 141C) in color; medium pubescence.

*Pollen.*—Yellow (RHS 11B) in color.

*Fragrance.*—Slight.

*Bloom season.*—Mid-season, full bloom observed on Oct. 14, 2007 in Drouin Victoria, Australia.

Fruit: (Observations from a limited number of typical fruit in the laboratory).

*Size.*—medium, about 3.1 inches long and 3 inches wide.

*Form.*—Conical globose.

*Cavity.*—1.1 inches wide and 0.5 inches deep.

*Basin.*—About 0.4 inch deep and about 1.1 inch wide; pubescence observed weak or absent.

*Stem.*—Medium thickness; typical average observed in 10 fruit, about 0.75 inch long and 0.085 inch in diameter; Greyed Purple (RHS 183A) in color.

*Locules.*—Five Open locules per fruit.

*Skin.*—Intensity of colour is bright.

*Lenticels.*—Medium in number, Yellow-White (RHS 158B).

*Color.*—General color effect: Solid Red Flush with Stripes, red in colour over 95% of the fruit. Ground color: Greyed Red (RHS 180B). Overcolor: Red (RHS 46A). Russetting: Cheeks, absent, Cavity present, Eye absent.

*Fruit properties at maturity* (*based on* 10 *fruit tested in the laboratory*).—Acid content: About 160 mg per liter malic acid. Firmness: About 8.7 kg to 10.3 kg, averaging about 9.6 kg. Soluble solids: About 12.0 to 14.0%, averaging about 12.9%. Starch index: On scale of 1 (high starch) to 6 (low starch), range 2 to 3, average about 2.5. Flavor: Sweet. Juiciness: Juicy. Flesh color: Cream (RHS 8D). Aroma: Present.

*Fruit production.*—First picking date in 2008 in Victoria, Australia, was about February 20$^{th}$ and last picking date was about February 29$^{th}$; average production was 50 kg of fruit per tree.

*Storage.*—Fruit remains fresh at room temperature for seven days, and can be stored up to three months in cold storage (34° F.).

*Core.*—Median bundle area shape; about 1.55 inches long and about 1.25 inches wide.

*Seed.*—About 1.3 seeds per cell; Acute shaped; about 0.43 inch long and about 0.24 inch wide; Purple (RHS N77A) in color.

*Harvest dates.*—Comparative data shown in Table 1

TABLE 1

Harvest dates for 'Alvina' and other Gala varieties in Drouin, Victoria.

| Variety | 2006 harvest dates | 2007 harvest dates |
|---|---|---|
| 'Galaxy' Gala (U.S. Plant Pat. No. 6,955) | Feb. 9 | Feb. 22 |
| 'Royal' Gala (U.S. Plant Pat. No. 4,121) | Feb. 22 | Feb. 26 |
| 'Alvina' Gala | Feb. 7 | Feb. 19 |

*Usage.*—Fresh consumption.

I claim:

1. A new and distinct variety of apple tree, substantially as herein shown and described.

* * * * *